(12) United States Patent
Colbert

(10) Patent No.: US 11,234,585 B2
(45) Date of Patent: Feb. 1, 2022

(54) DENTAL RETRACTION AND ISOLATION DEVICES

(71) Applicant: E. Lynn Colbert, Boulder, CO (US)

(72) Inventor: E. Lynn Colbert, Boulder, CO (US)

( * ) Notice: Subject to any disclaimer, the term of this patent is extended or adjusted under 35 U.S.C. 154(b) by 338 days.

(21) Appl. No.: 16/452,296

(22) Filed: Jun. 25, 2019

(65) Prior Publication Data

US 2020/0405139 A1 Dec. 31, 2020

(51) Int. Cl.
*A61B 1/24* (2006.01)
*A61B 13/00* (2006.01)

(52) U.S. Cl.
CPC ............. *A61B 1/24* (2013.01); *A61B 13/00* (2013.01)

(58) Field of Classification Search
CPC .. A61B 1/24; A61B 13/00; A61B 1/32; A61C 17/10; A61C 5/80; A61C 5/90; A61C 5/82
USPC ........................................ 433/136, 138, 140
See application file for complete search history.

(56) References Cited

U.S. PATENT DOCUMENTS

| | | | | |
|---|---|---|---|---|
| 641,170 A * | 1/1900 | Thurmond et al. | ...... | A61C 5/90 433/140 |
| 1,400,854 A * | 12/1921 | Barr | ......... | A61B 1/24 600/242 |
| 2,680,908 A * | 6/1954 | Daigle | ...... | A61C 5/80 433/136 |
| 2,897,597 A * | 8/1959 | Ivory | ...... | A61C 19/001 433/138 |
| 3,396,468 A * | 8/1968 | Dayhoff | ...... | A61C 5/82 433/93 |
| 3,916,880 A * | 11/1975 | Schroer | ...... | A61B 1/24 600/205 |
| 4,053,984 A * | 10/1977 | Moss | ...... | A61B 1/24 433/93 |
| 4,992,046 A * | 2/1991 | Sharp | ...... | A61C 17/08 433/93 |
| 5,037,298 A * | 8/1991 | Hickham | ...... | A61C 17/10 433/93 |
| 5,199,872 A | 4/1993 | Leal | | |
| 5,516,286 A * | 5/1996 | Kushner | ...... | A61C 5/80 433/93 |
| 6,213,772 B1 | 4/2001 | Costello | | |
| 7,785,105 B2 * | 8/2010 | Anderson | ...... | A61C 17/08 433/140 |
| 8,376,743 B1 * | 2/2013 | Bukhary | ...... | A61B 1/24 433/140 |
| 9,387,054 B2 | 7/2016 | Hines et al. | | |

(Continued)

*Primary Examiner* — Nicholas D Lucchesi
(74) *Attorney, Agent, or Firm* — Elevated IP, LLC

(57) ABSTRACT

Dental retraction and isolation devices disclosed herein simultaneously isolate at least a portion of a maxillary dental arch and at least a portion of an opposing mandibular dental arch, along with the gingivae near the gumline, while gently retracting a patient's tongue, cheek and lips. All procedures in operative dentistry and fixed prosthodontics can be performed using these devices, but they are particularly useful where access to the gingiva is necessary or desirable, where a dry field is crucial for bonding success, and/or where occlusion and masticatory movement in a dry field are advantageous. The devices can be deployed in seconds and stay in place without clamps, ligatures or wedges, and because the devices are fabricated from soft, pliable materials, they reduce tissue damage and conform to oral surfaces.

20 Claims, 13 Drawing Sheets

(56) References Cited

U.S. PATENT DOCUMENTS

| | | | |
|---|---|---|---|
| 2004/0005529 A1* | 1/2004 | O'Neill | A61B 1/24 433/140 |
| 2005/0227199 A1* | 10/2005 | Patrickus | A61C 17/10 433/93 |
| 2006/0234187 A1* | 10/2006 | Kilcher | A61C 5/90 433/140 |
| 2007/0218422 A1* | 9/2007 | Ehrenfeld | A61C 5/90 433/140 |
| 2008/0064001 A1* | 3/2008 | Dorfman | A61C 5/90 433/29 |
| 2010/0291503 A1* | 11/2010 | Shih | A61B 90/16 433/31 |
| 2016/0270880 A1 | 9/2016 | Hines et al. | |
| 2017/0333159 A1* | 11/2017 | Pietarinen | A61C 5/90 |

\* cited by examiner

DENTAL RETRACTION AND ISOLATION DEVICES

CROSS-REFERENCE TO RELATED APPLICATIONS

None.

STATEMENT REGARDING GOVERNMENT FUNDING

None.

BACKGROUND

In dental procedures requiring isolation, the use of rubber dams held in position by tooth clamps and stretched across rigid or semi-rigid frames is the current industry standard. Rubber dams are, however, susceptible to tearing in the presence of sharp instruments, and they may obstruct breathing and/or press a patient's tongue into a position that activates the gag reflex. Rubber dams also do not allow access to the gingivae, making them unsuitable for crown and bridge, restorations near the gum line, and other procedures involving the gingivae or root surfaces.

For soft tissue procedures, retraction is typically accomplished using a hard metallic or plastic device. But such devices prevent occlusion and masticatory movement, making it necessary to insert and remove the retractor multiple times during a procedure to evaluate and adjust a patient's bite, whereby a dry field cannot be maintained. Also, this repetitive intrusion and removal increases the chance that the soft tissues of the oral cavity will be abraded or cut, which increases the risk of infection. Infection risk is exacerbated when the retraction device includes ports, orifices, channels or other non-sterilizable features.

In addition to commercially available products, US Patent Pub. No. 2016/0270880 and U.S. Pat. Nos. 9,387,054, 6,213,772 and 5,199,872 disclose dental isolation and/or retraction devices. However, all of these products suffer from one or more of the disadvantages discussed above.

SUMMARY

Dental devices disclosed herein can be deployed in seconds and stay in place without clamps, ligatures or wedges. The devices are fabricated from soft, pliable materials to reduce tissue damage and risk of infection, to better conform to oral surfaces over time, and to permit occlusion and masticatory movement. The devices simultaneously isolate at least a portion of a maxillary dental arch and at least a portion of an opposing mandibular dental arch, along with the gingivae near the gum line, while retracting a patient's tongue, cheek and lips. However, since the devices are flexible, articulation and independent movement of the upper and lower jaws is possible.

All procedures in operative dentistry can be performed in a field free of saliva and intrusion from tongue, lip or cheek using the dental devices disclosed herein. Class II (interproximal) and class V (cervical) restorations, crown preparation, full-quadrant crown preparation, placement of retraction cord, laser scanning and crown or inlay cementation, and full-mouth reconstruction are all possible. The disclosed devices are particularly useful where a dry field is crucial for bonding success, for example, pit and fissure sealants. Bonding of composite, ceramic or zirconia can be accomplished in a dry field in all teeth, even the most posterior molars, where maintaining a dry field has been historically difficult. The present devices isolate the teeth at the level of the attached gingiva so that, even teeth that are broken off at the gum line can be restored with bonded restorations, because a dry field can be maintained. These, and other, advantages will become apparent from the present disclosure.

In an aspect, a dental device comprises a frame forming a first saddle for at least partially surrounding a portion of a dental arch, a second saddle for at least partially surrounding a portion of an opposing dental arch, a buccal bow, and first and second extraoral spacers connecting anterior, buccal regions of the first and second saddles with first and second ends of the buccal bow and a membrane within an intraspacer area of the frame.

In an embodiment, a dental device disclosed herein is configured for unilateral placement. In an embodiment, a dental device configured for unilateral placement is reversible, i.e., a device that fits one side of a patient's mouth can be rotated 180 degrees to fit the other side of the patient's mouth. In an embodiment, a dental device is symmetrical across a horizontal plane.

In an embodiment, the first saddle, the first spacer, and the first end of the buccal bow of a dental device comprise a substantially planar S-shaped configuration and/or the second saddle, the second spacer, and the second end of the buccal bow of the dental device comprise a substantially planar S-shaped configuration.

In an embodiment, lingual regions of the first and second saddles are joined by a lingual bow of the frame. In an embodiment the lingual bow is substantially planar and oriented substantially perpendicularly to the first and second saddles. In an embodiment, the lingual bow is substantially U-shaped with a closed end of the "U" disposed within a posterior region of the device or within an anterior region of the device.

In an embodiment, the frame is contiguous. In an embodiment, the frame is a single loop. In an embodiment, the frame is flexible. In an embodiment, the frame is configured to permit engagement of upper and lower occlusal tooth surfaces when the frame is positioned within an oral cavity. In an embodiment, the frame is a metal or plastic wire coated with silicone, nitrile, rubber or combinations thereof.

In an embodiment, the first and/or second spacer has a length between 0.5 cm and 3.0 cm, or between 0.5 cm and 2.0 cm, or between 0.75 cm and 1.5 cm. In an embodiment, a longitudinal axis of the first and/or second spacer is substantially perpendicular to a plane of the buccal bow.

In an embodiment, the buccal bow is partially or completely extraoral. In an embodiment, the buccal bow is partially or completely intraoral. In an embodiment, the buccal bow is configured to reside partially or completely outside an oral cavity or the buccal bow is configured to reside partially or completely inside an oral cavity. In an embodiment, the buccal bow is substantially U-shaped with a closed end of the "U" disposed within a posterior region of the device or within an anterior region of the device. In an embodiment, the buccal bow is substantially planar and oriented substantially perpendicularly to a longitudinal axis of the first and/or second saddle.

In an embodiment, at least one elastomeric blade extends from the first saddle toward an interior region of the first saddle and/or the second saddle toward an interior region of the second saddle. In an embodiment, an elastomeric blade is a wedge-shaped blade that extends from the saddle and narrows toward an interior region of the saddle. In an embodiment, an elastomeric blade extends along the entire interior edge of the saddle. In an embodiment, the elastomer is selected from the group consisting of rubber, silicone rubber, polyvinylsiloxane, polydimethylsiloxane (PDMS), neoprene and combinations thereof.

In an embodiment, a membrane extends into an inter-saddle area, an intra buccal bow area, an intra lingual bow area and/or an anterior palatal—lingual space. In an embodiment, the membrane comprises at least one aperture to allow a patient to breathe. In an embodiment, the membrane comprises a material selected from the group consisting of rubber, silicone, nitrile, polyetheretherketone (PEEK), polyarylamide, polyethylene, polysulphone and combinations thereof.

In an embodiment, a dental device is configured for bilateral placement and a frame further comprises a third saddle joined lingually to the first saddle, a fourth saddle joined lingually to the second saddle, a second buccal bow, and third and fourth extraoral spacers connecting anterior, buccal regions of the third and fourth saddles with first and second ends of the second buccal bow.

In an embodiment, the third saddle, the third spacer, and the first end of the second buccal bow comprise a substantially planar S-shaped configuration and/or the fourth saddle, the fourth spacer, the second end of the second buccal bow comprise a substantially planar S-shaped configuration.

In an embodiment, at least one elastomeric blade extends from the third saddle toward an interior region of the third saddle and/or the fourth saddle toward an interior region of the fourth saddle.

In an embodiment, a dental device is symmetrical across a horizontal plane and a vertical plane.

In an embodiment, a dental device does not comprise ports or orifices. In an embodiment, a dental device is cleansable, autoclavable, sterilizable and/or reusable. In an embodiment, a dental device is disposable.

In an embodiment, any of the dental devices disclosed herein can be manufactured in various sizes, such as pedodontic, small, medium, large or extra-large sizes to accommodate various sized oral cavities. Further, sizing of a dental device as disclosed herein may be adjusted to fit the oral cavity of a non-human animal.

In an aspect, a method of making a dental device comprises providing a frame forming a first saddle for at least partially surrounding a portion of a dental arch, a second saddle for at least partially surrounding a portion of an opposing dental arch, a buccal bow, and first and second extraoral spacers connecting anterior, buccal regions of the first and second saddles with first and second ends of the buccal bow and filling an intra-spacer area of the frame with a membrane.

In an aspect, a method of using a dental device comprises at least partially compressing a frame forming a first saddle for at least partially surrounding a portion of a dental arch, a second saddle for at least partially surrounding a portion of an opposing dental arch, a buccal bow, and first and second extraoral spacers connecting anterior, buccal regions of the first and second saddles with first and second ends of the buccal bow and a membrane within an intra-spacer area of the frame, positioning the frame in a patient's oral cavity and allowing the frame to expand.

DETAILED DESCRIPTION

Figure 1:
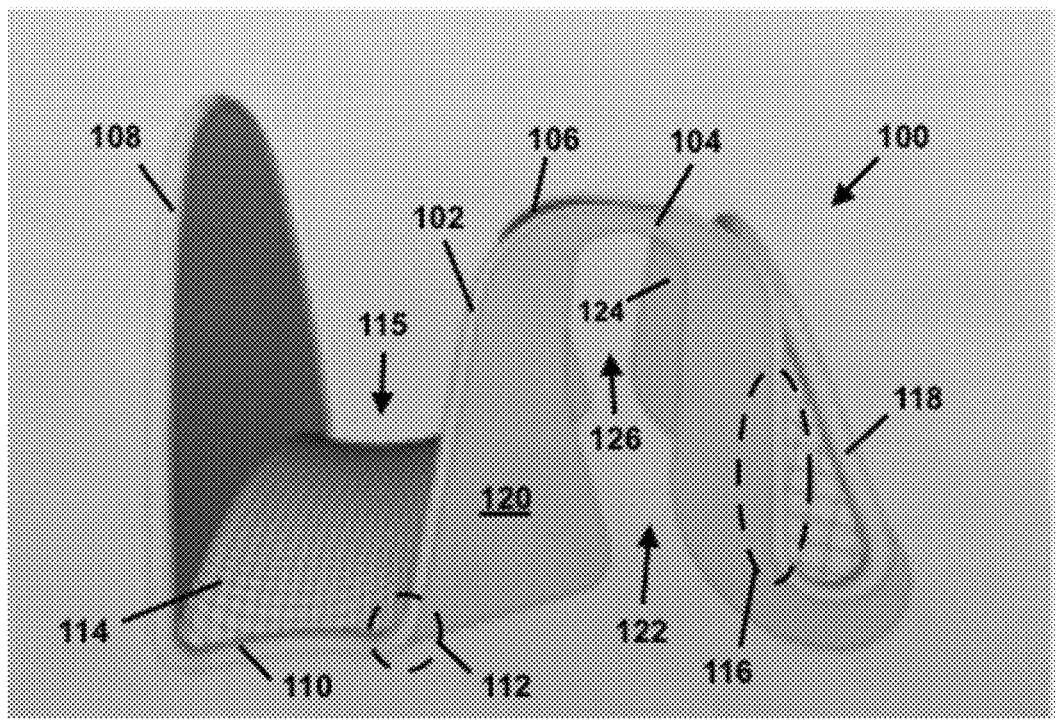
FIG. 1 provides a superior or inferior view of a dental retraction and isolation device configured for unilateral placement in an oral cavity, according to an embodiment.
Figure 1:
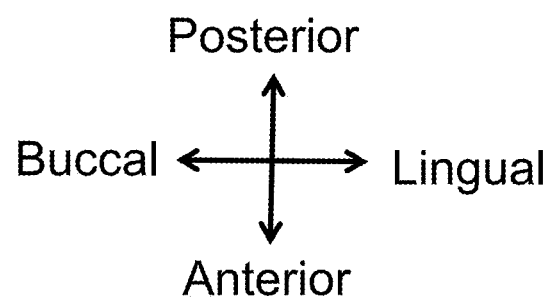

In general, the terms and phrases used herein have their art-recognized meaning, which can be found by reference to standard texts, journal references and contexts known to those skilled in the art. The following definitions are provided to clarify their specific use in the context of this description.

The dental devices disclosed herein are described by anatomical reference assuming proper placement of the device within a patient's oral cavity. It should be understood, however, that a device need not be located within an oral cavity for the present descriptions to accurately describe the relative locations of components forming the devices.

As used herein, an "oral cavity" refers to the cavity of the mouth, including the lips, hard palate, soft palate, retromolar trigone, front two-thirds of the tongue, gingiva, buccal mucosa, and floor of the mouth under the tongue.

As used herein, "anterior" refers to the front of a patient or a position near the front of a patient. With respect to an oral cavity, an anterior position is near the mouth opening.

As used herein, "posterior" refers to the back or hind of a patient or a position near the back or hind of a patient. With respect to an oral cavity, a posterior position is near the throat.

As used herein, "buccal" refers to a position near a patient's cheek or on the cheek side of the oral cavity (i.e., on the outside of the molars).

As used herein, "lingual" refers to a position near a patient's tongue or on the tongue side of the oral cavity (i.e., on the inside of the molars).

As used herein, "oral" refers to the mouth. Thus, a device or component that is "extraoral" is configured for placement outside the mouth or oral cavity.

A "device" is a combination of components operably connected to produce one or more desired functions.

A "component" is used broadly to refer to an individual part of a device.

The terms "direct and indirect" describe the actions or physical positions of one object relative to another object. For example, an object that "directly" acts upon or touches another object does so without intervention from an intermediary. Contrarily, an object that "indirectly" acts upon or touches another object does so through an intermediary (e.g., a third object).

A "predetermined" location refers to the position of an object, plane, surface or material within an object that is set or determined prior to fabrication and achieved during fabrication.

"Contiguous" refers to materials or layers that are touching or connected throughout in an unbroken sequence.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyethylene terephthalate, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material that can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Exemplary elastomers include, but are not limited to silicon containing polymers such as polysiloxanes including poly(dimethyl siloxane) (i.e. PDMS and h-PDMS), poly(methyl siloxane), partially alkylated poly (methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones.

Figure 7:
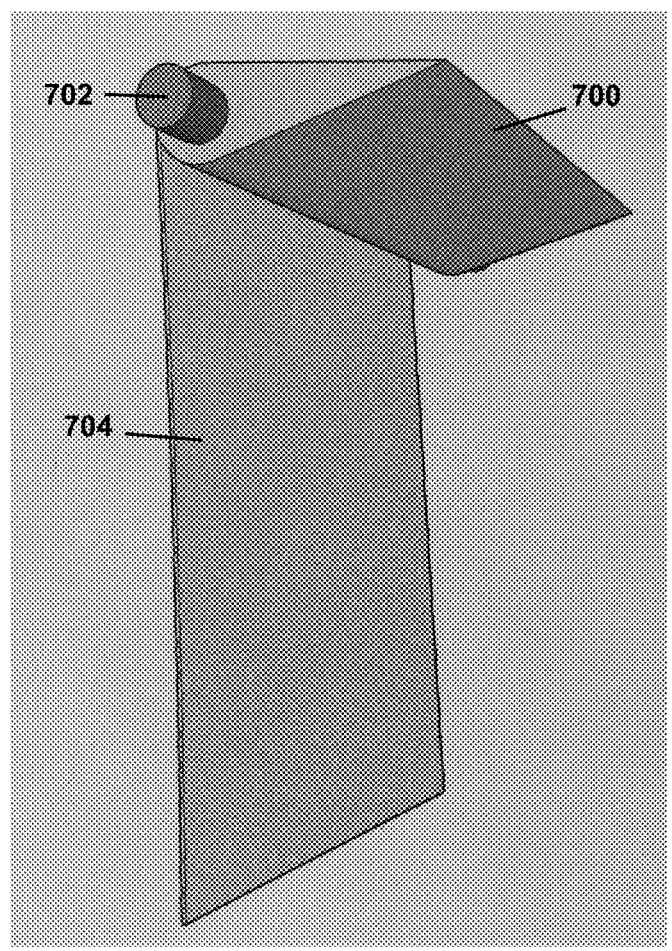
FIG. 7 provides a cut-away view of an exemplary blade encapsulating a portion of a frame of a dental device, according to an embodiment.

FIG. 1 provides a superior or inferior view of an exemplary dental retraction and isolation device 100 configured for unilateral placement in a patient's oral cavity. An anatomical coordinate system indicates the positioning of device 100 when properly positioned within the patient's oral cavity. Device 100 includes a frame 102 forming a first saddle 104 for at least partially surrounding a portion of a dental arch, a second saddle 106 for at least partially surrounding a portion of an opposing dental arch, a buccal bow 108, and first 110 and second extraoral spacers connecting anterior, buccal regions 112 of the first 104 and second 106 saddles with first and second ends of the buccal bow. An optional membrane 114 is disposed within at least a portion of an intra-spacer area 115 of frame 102. As shown, lingual regions 116 of the first 104 and second 106 saddles are joined by a lingual bow 118 of frame 102. Lingual bow 118 retracts the patient's tongue from the operable area while maintaining normal antero-posterior movement of the tongue. Allowing for antero-posterior movement of the tongue prevents displacement of device 100 by the tongue and allows for normal mouth breathing and use of sedation without concern about adequate oxygenation. Device 100 also includes an elastomeric blade 120 extending from first saddle 104 toward an interior region 122 of the first saddle and an elastomeric blade 124 extending from second saddle 106 toward an interior region 126 of the second saddle. As shown in FIGS. 3 and 7 elastomeric blades 120, 124 are wedge-shaped and extend from saddles 104, 106 and narrow toward interior regions 122, 126.

Figure 2A:
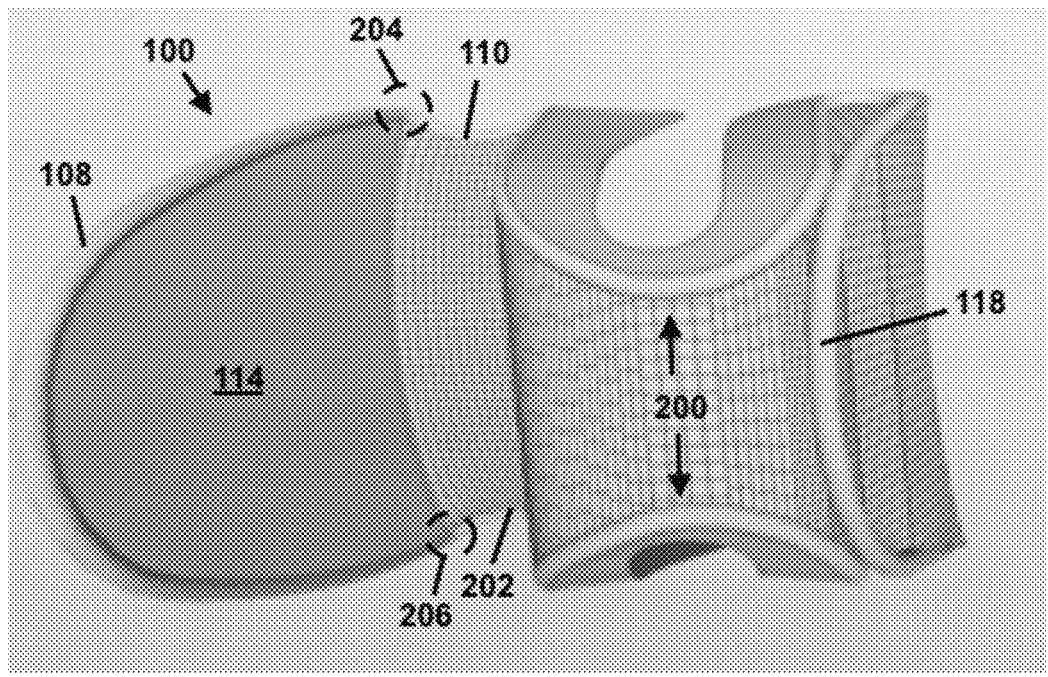
FIGS. 2A and 2B provide posterior views of the dental device of FIG. 1.
Figure 2B:
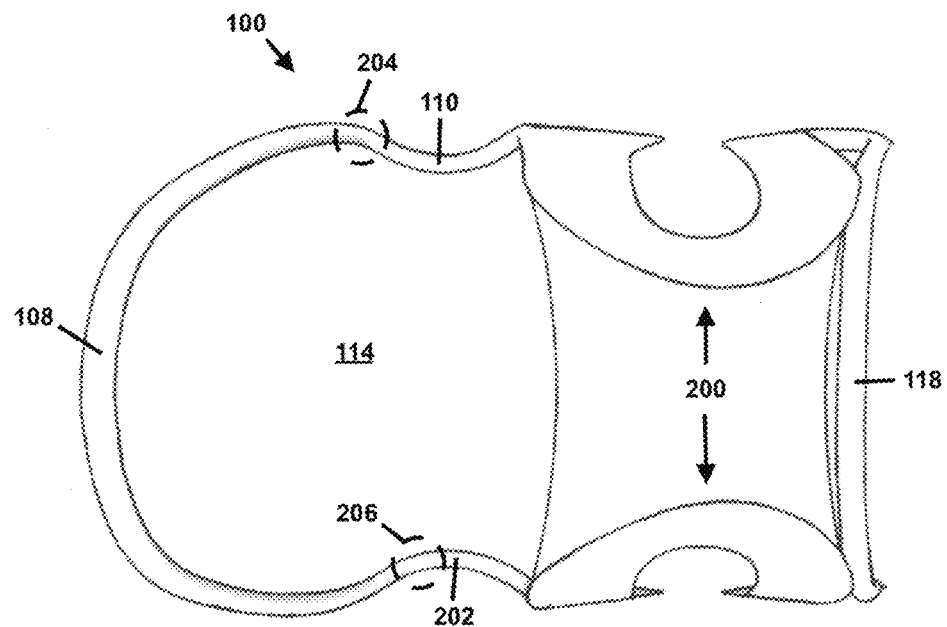

FIGS. 2A and 2B provide posterior views of dental device 100 showing greater detail of the inter-saddle area 200 of membrane 114. Membrane 114 may terminate within lingual bow 118 and mayor may not extend into buccal bow 108. FIGS. 2A and 2B also show first 110 and second 202 extraoral spacers connecting anterior, buccal regions of the first and second saddles with first 204 and second 206 ends of buccal bow 108, which is configured for extraoral placement, e.g., on or near an external surface of the patient's cheek.

Figure 3A:
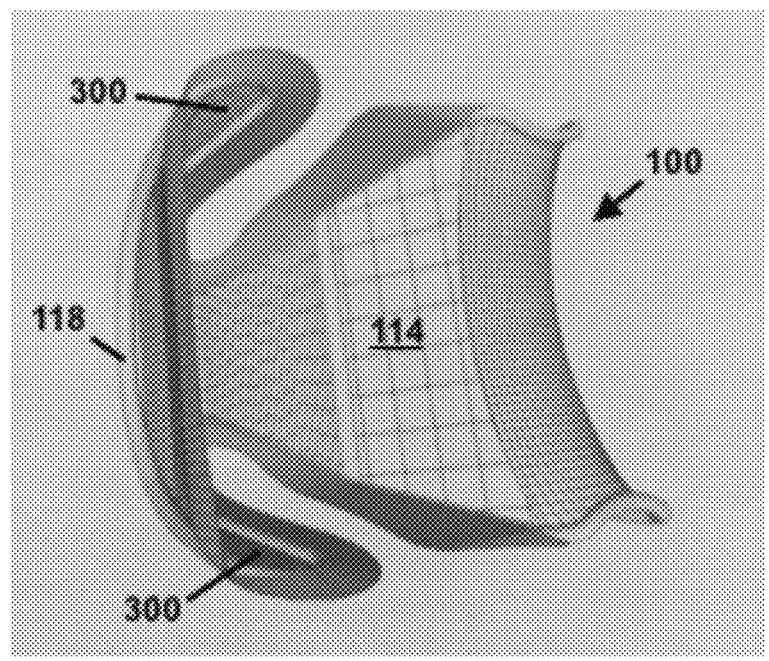
FIGS. 3A and 3B provide anterolingual views of the dental device of FIG. 1.
Figure 3B:
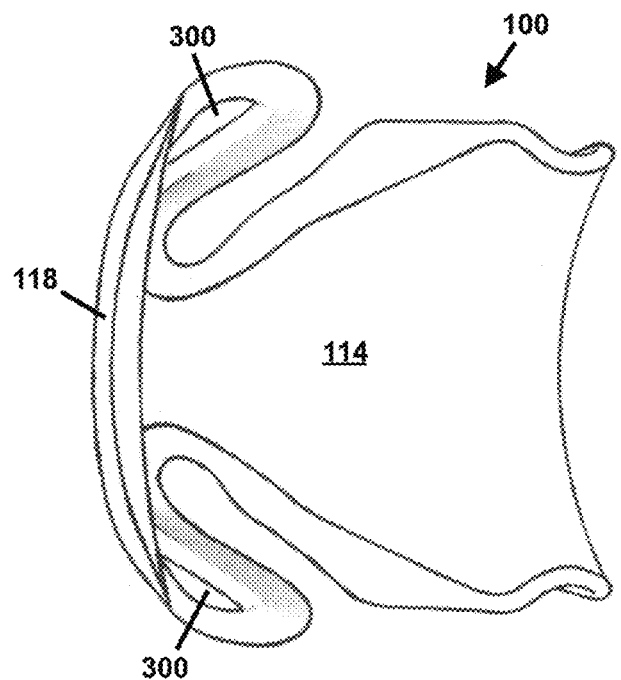

FIGS. 3A and 3B provide anterolingual views of dental device 100 showing greater detail of membrane 114 terminating within lingual bow 118 and extending into anterior palatal—lingual spaces 300. Termination of membrane 114 within lingual bow 118 improves flexibility of device 100, particularly, the ability of the patient to occlude the upper and lower tooth surfaces, while extension of membrane 114 into anterior palatal-lingual spaces 300 maintains isolation while providing greater retraction between the tongue and the operable area.

Figure 3C:
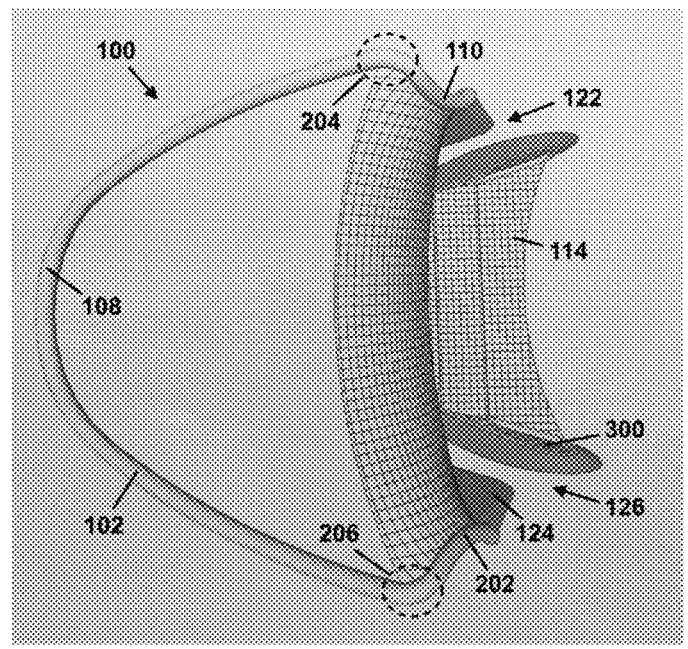
FIGS. 3C and 3D provide anterobuccal views of the dental device of FIG. 1.
Figure 3D:
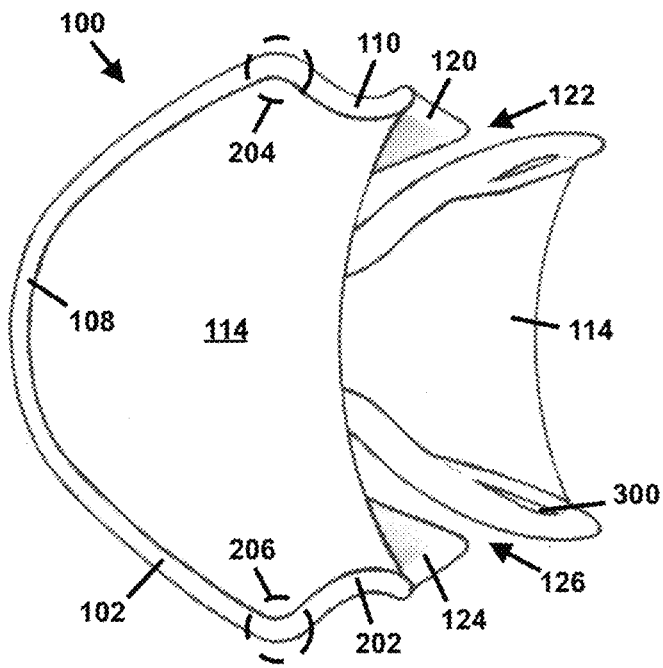

FIGS. 3C and 3D provide anterobuccal views of dental device 100 including a membrane 114 that partially or completely fills the area within buccal bow 108. The joinder of first 204 and second 206 ends of buccal bow 108 to first 110 and second 202 extraoral spacers is clearly visible.

Figure 4A:
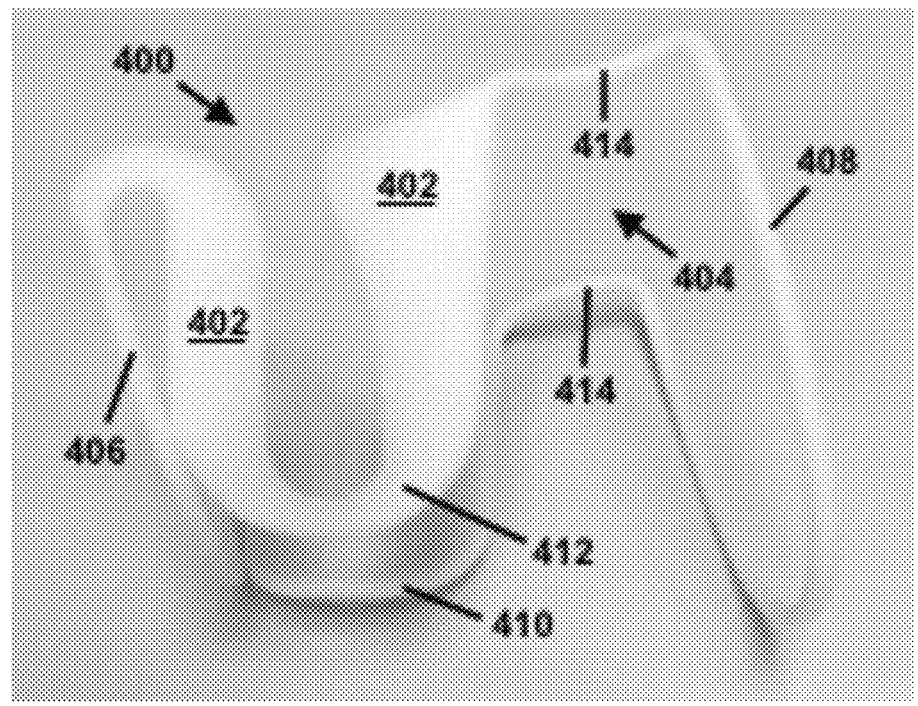
FIGS. 4A and 4B provide superior or inferior views of a frame with blades for a dental device, according to an embodiment.
Figure 4B:
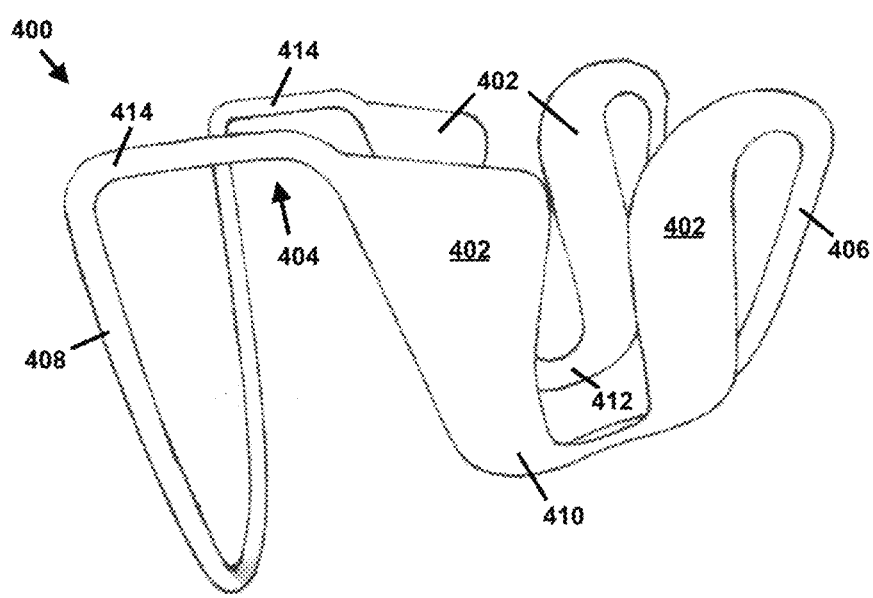

FIGS. 4A and 4B provide superior or inferior views of a frame 400 comprising blades 402 configured for unilateral placement in a patient's oral cavity. As shown, frame 400 is contiguous and forms a single loop, which defines an intra-frame space 404. Frame 400 includes a lingual bow 406 and an extraoral buccal bow 408, which are both substantially planar and oriented substantially perpendicularly to first 410 and second 412 saddles of the frame. In the embodiment shown, frame 400 is contiguous with blades 402. However, blades 402 may be distinct from frame 400 and fabricated from a different material than frame 400 (see, e.g., FIG. 7).

Figure 5A:
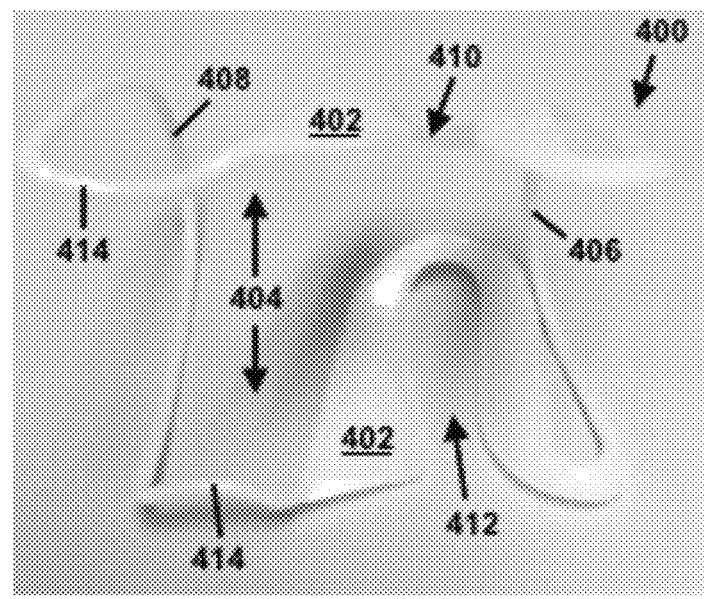
FIGS. 5A and 5B provide anterior views of the frame of FIGS. 4A and 4B.
Figure 5B:
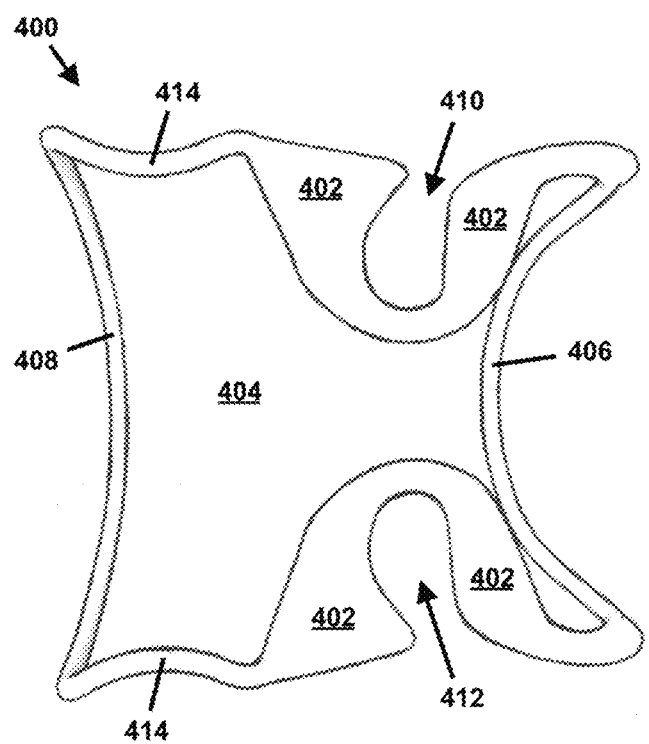
Figure 5C:
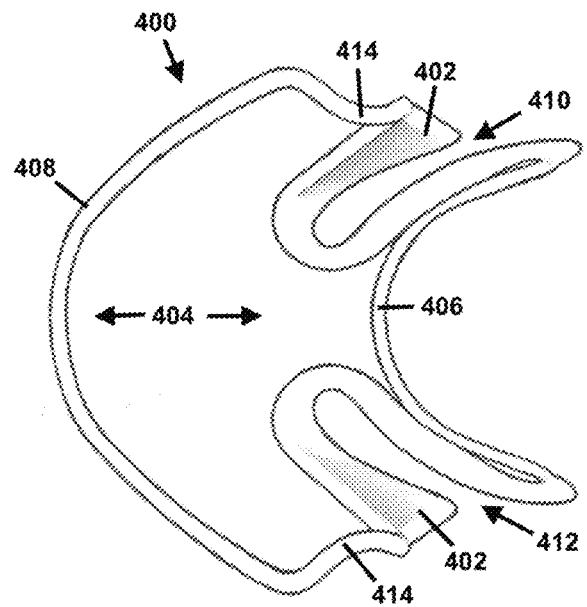
FIGS. 5C and 5D provide anterobuccal and anterolingual views of the frame of FIGS. 5A and 5B.
Figure 5D:
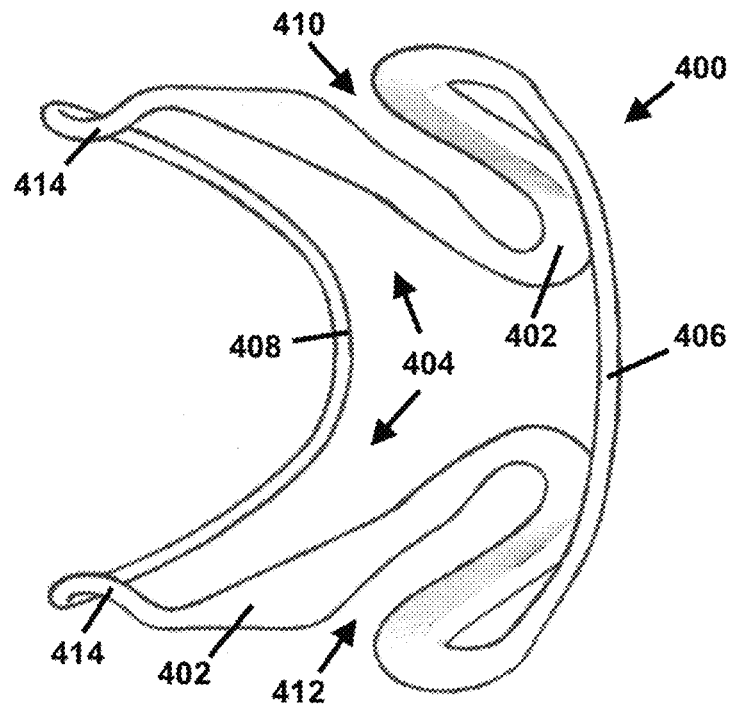

FIGS. 5A and 5B provide anterior views of frame 400 of FIGS. 4A and 4B. It is apparent from this view that the upper and lower halves of the dental device are identical making it symmetrical across a horizontal plane. FIGS. 5C and 5D provide anterobuccal and anterolingual views of frame 400, respectively. Again, the symmetry of frame 400 across a horizontal plane is visible.

Figure 6A:
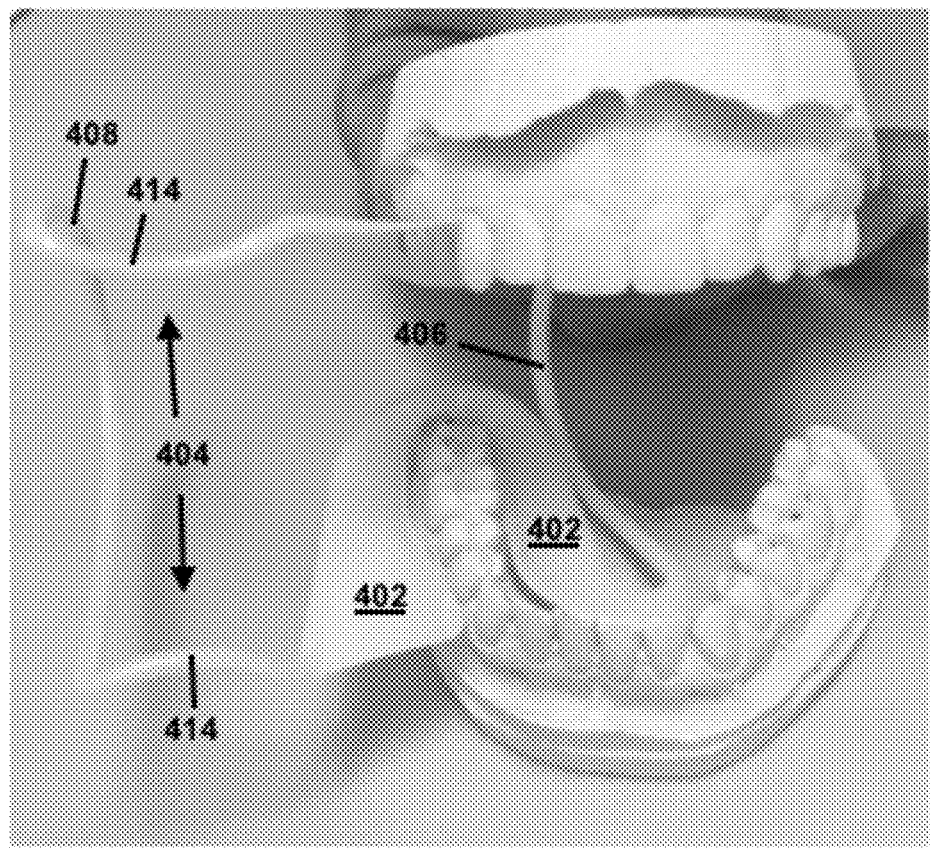
FIGS. 6A and 6B provide views of the frame of FIGS. 4A, 4B and 5A-5D unilaterally positioned to at least partially surround portions of opposing dental arches, according to an embodiment.
Figure 6B:
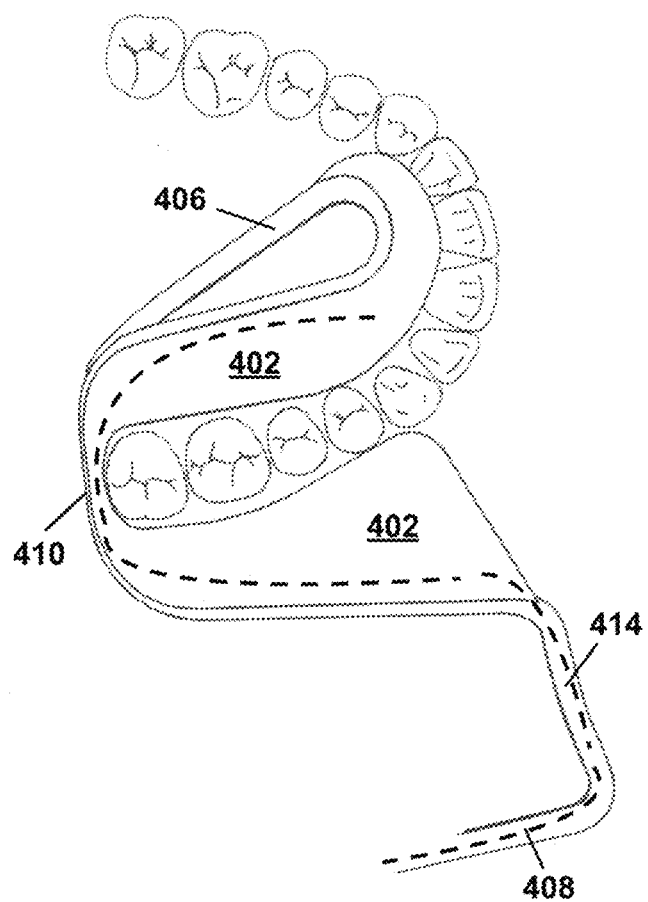

FIGS. 6A and 6B provide views of frame 400 of FIGS. 4A, 4B and 5A-5D unilaterally positioned to at least partially surround portions of opposing dental arches. This view illustrates an embodiment where the buccal bow and lingual bow are narrowest and hinged posteriorly and widen anteriorly. This configuration provides anteroposterior pressure that gently opens a patient's jaw consistent with its natural physiology. FIG. 6B shows that each saddle 410, spacer 414, and end of buccal bow 408 are configured substantially in an S-shape (dashed line).

FIG. 7 provides a cut-away view of an exemplary blade 700 encapsulating a portion of a frame 702 of a dental device. In this example, blade 700 and frame 702 are made from distinct materials. For example frame 702 may be a metal or plastic wire coated with silicone, nitrile, rubber or a combination thereof, whereas blade 700 may be an elastomer selected from the group consisting of rubber, silicone rubber, polyvinylsiloxane, polydimethylsiloxane (PDMS), neoprene and combinations thereof. An isolating membrane 704 may extend from blade 700 or frame 702. Typically, membrane 704 comprises a material selected from the group consisting of rubber, silicone, nitrile, polyetheretherketone (PEEK), polyarylamide, polyethylene, polysulphone and combinations thereof.

Figure 8:
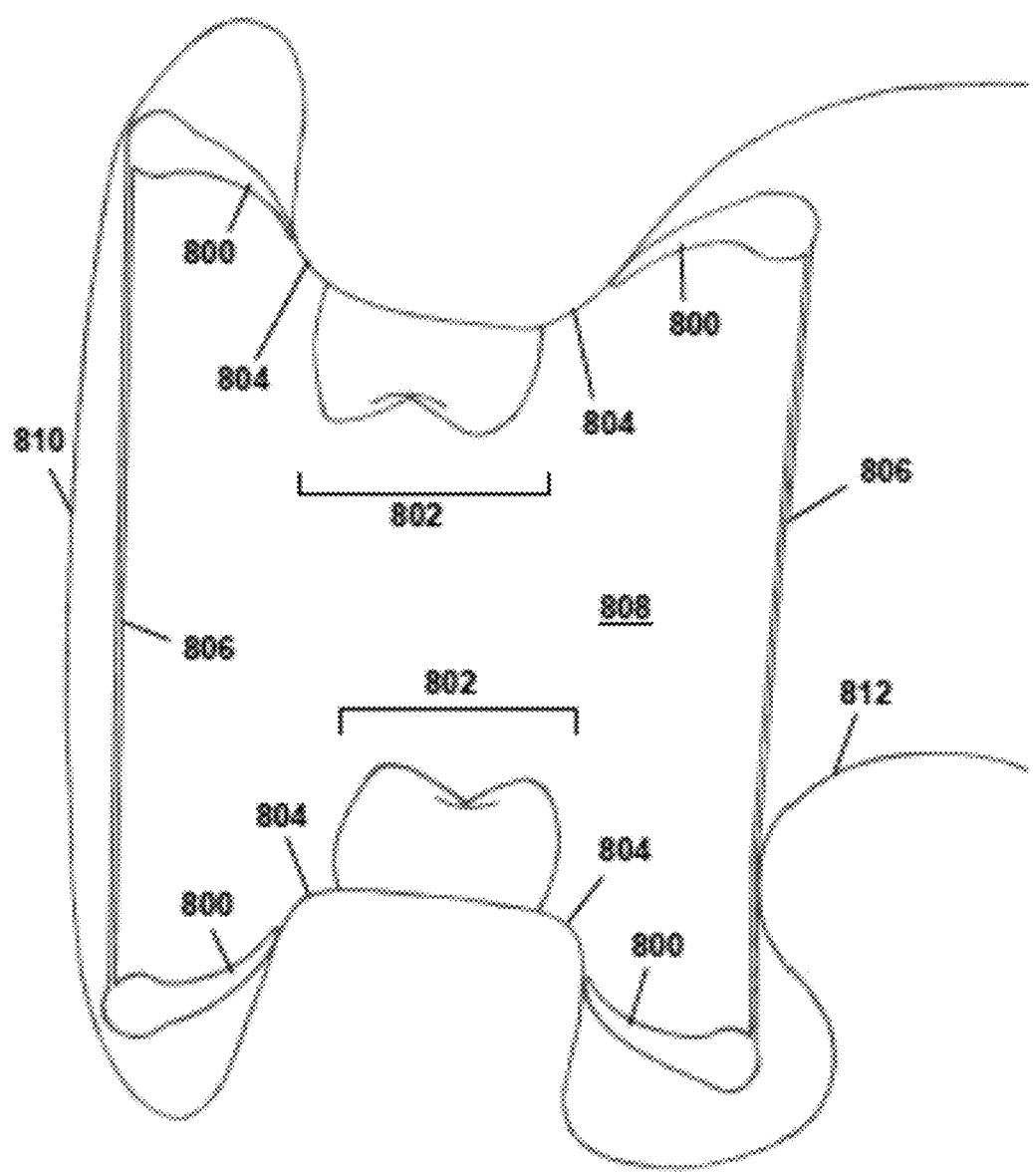
FIG. 8 provides a cross sectional view illustrating how flexible blades of a dental device isolate a portion of a dental arch, while simultaneously allowing access to the gingivae, according to an embodiment.

FIG. 8 provides a cross sectional view illustrating how flexible blades 800 of a dental device, such as device 100 of FIG. 1, isolate a portion of a dental arch 802, while simultaneously allowing access to the gingivae 804. Isolation is created by a membrane 806 separating the operable area 808 from buccal 810 and lingual 812 tissue.

Figure 9:
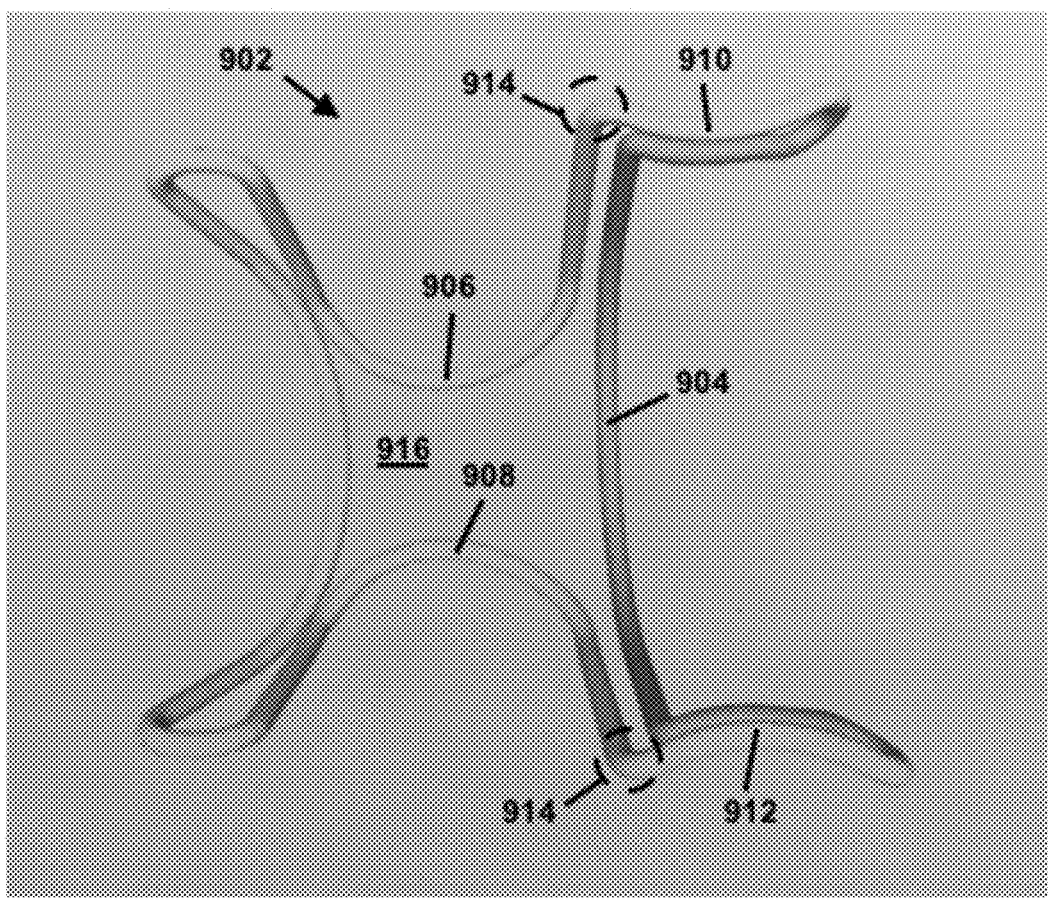
FIG. 9 provides a schematic of a frame forming an internal buccal bow, according to an embodiment.

FIG. 9 provides a schematic of a frame 902 forming an intraoral buccal bow 904 of a dental device. As with previous examples, frame 902 forms a first saddle 906, a second saddle 908, and first 910 and second 912 extraoral spacers connecting anterior, buccal regions 914 of the first 906 and second 908 saddles with first and second ends of buccal bow 904. A dental device comprising frame 902 may include one or more elastomeric blades within the first 906 and/or second 908 saddle and a membrane within at least a portion of an intra-frame space 916.

Figure 10:
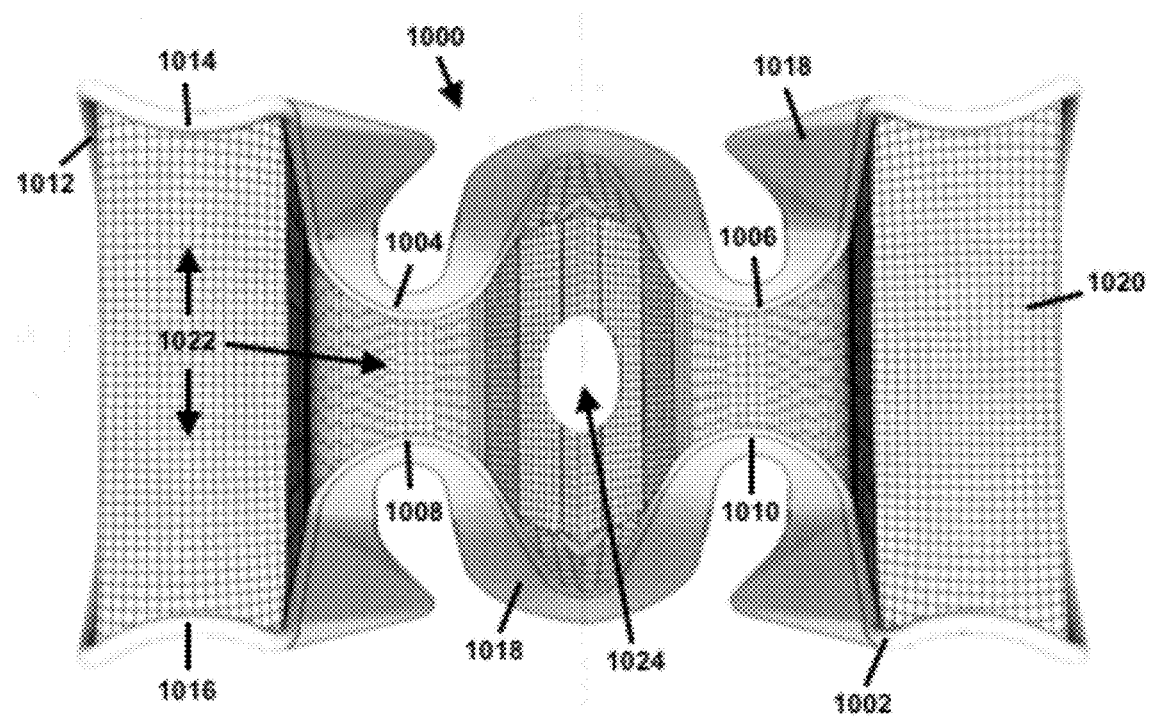
FIG. 10 provides an anterior view of a dental retraction and isolation device configured for bilateral placement in an oral cavity, according to an embodiment.

FIG. 10 provides an anterior view of an exemplary dental retraction and isolation device 1000 configured for bilateral placement in a patient's oral cavity. In the bilateral version, frame 1002 comprises a third saddle 1004 joined lingually to a first saddle 1006, a fourth saddle 1008 joined lingually to a second saddle 1010, a second buccal bow 1012, and third 1014 and fourth 1016 extraoral spacers connecting anterior, buccal regions of the third 1004 and fourth 1008 saddles with first and second ends of the second buccal bow 1012. A plurality of elastomeric blades 1018 extend from each saddle toward an interior region of the respective saddle and a membrane 1020 at least partially occupies an intra-frame space 1022. As shown, the membrane 1020 comprises at least one aperture 1024 to allow a patient to breathe. It is apparent from FIG. 10 that the upper and lower halves of the dental device are identical and the left and right halves of the dental device are symmetrical, making the entire device symmetrical across both horizontal and vertical planes.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps. All art-known functional equivalents of materials and methods are intended to be included in this disclosure.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

It must be noted that as used herein and in the appended claims, the singular forms "a", "an", and "the" include plural reference unless the context clearly dictates otherwise. Thus, for example, reference to "a blade" includes a plurality of such blades and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

What is claimed is:

1. A dental device comprising:
   a frame forming a first saddle for at least partially surrounding a portion of a dental arch, a second saddle for at least partially surrounding a portion of an opposing dental arch, a buccal bow, and first and second extraoral spacers connecting anterior, buccal regions of the first and second saddles with first and second ends of the buccal bow; and
   a membrane within an intra-spacer area of the frame.

2. The dental device of claim 1, wherein the device is configured for unilateral placement.

3. The dental device of claim 1, wherein the device is symmetrical across a horizontal plane.

4. The dental device of claim 1, wherein the first saddle, the first spacer, and the first end of the buccal bow comprise a substantially planar S-shaped configuration and/or wherein the second saddle, the second spacer, and the second end of the buccal bow comprise a substantially planar S-shaped configuration.

5. The dental device of claim 1, wherein lingual regions of the first and second saddles are joined by a lingual bow of the frame.

6. The dental device of claim 5, wherein the lingual bow is substantially planar and oriented substantially perpendicularly to the first and second saddles.

7. The dental device of claim 1, wherein the frame is a single loop.

8. The dental device of claim 1, wherein the frame is flexible.

9. The dental device of claim 1, wherein the frame is configured to permit engagement of upper and lower occlusal tooth surfaces when the frame is positioned within an oral cavity.

10. The dental device of claim 1, wherein the first and/or second spacer has a length between 0.5 cm and 3.0 cm.

11. The dental device of claim 1, wherein a longitudinal axis of the first and/or second spacer is substantially perpendicular to a plane of the buccal bow.

12. The dental device of claim 1, wherein the buccal bow is partially or completely extraoral or wherein the buccal bow is partially or completely intraoral.

13. The dental device of claim 1, wherein the buccal bow is substantially planar and oriented substantially perpendicularly to a longitudinal axis of the first and/or second saddle.

14. The dental device of claim 1, wherein at least one elastomeric blade extends from the first saddle toward an interior region of the first saddle and/or the second saddle toward an interior region of the second saddle.

15. The dental device of claim 14, wherein the at least one elastomeric blade is a wedge-shaped blade that extends from (i) the first saddle and narrows toward the interior region of the first saddle and/or (ii) the second saddle and narrows toward the interior region of the second saddle.

16. The dental device of claim 14, wherein the at least one elastomeric blade extends along an entire interior edge of the first and/or the second saddle.

17. The dental device of claim 1, wherein the membrane extends into an inter-saddle area, an intra buccal bow area, an intra lingual bow area and/or an anterior palatal-lingual space.

18. The dental device of claim 1, wherein the frame further comprises:
   a third saddle joined lingually to the first saddle, a fourth saddle joined lingually to the second saddle, a second buccal bow, and third and fourth extraoral spacers connecting anterior, buccal regions of the third and fourth saddles with first and second ends of the second buccal bow; wherein the dental device is configured for bilateral placement.

19. The dental device of claim 18, wherein the membrane comprises at least one aperture to allow a patient to breathe.

20. The dental device of claim 18, wherein at least one elastomeric blade extends from the third saddle toward an interior region of the third saddle and/or the fourth saddle toward an interior region of the fourth saddle.

* * * * *